United States Patent [19]

Rhinehart et al.

[11] Patent Number: 5,365,928
[45] Date of Patent: Nov. 22, 1994

[54] ENDORECTAL PROBE WITH PLANAR MOVEABLE MRI COIL

[75] Inventors: Edward J. Rhinehart, Monroeville; Michael A. Spohn, Butler, both of Pa.

[73] Assignee: Medrad, Inc., Indianapola, Pa.

[21] Appl. No.: 982,177

[22] Filed: Nov. 25, 1992

[51] Int. Cl.⁵ .................... A61B 5/055; A61M 25/10
[52] U.S. Cl. .................... 128/653.5; 128/778; 604/96; 606/193; 606/197
[58] Field of Search ............... 128/653.2, 653.5, 772, 128/778; 606/191-194, 197; 604/95-96, 104, 55

[56] References Cited

U.S. PATENT DOCUMENTS

| | | |
|---|---|---|
| 4,276,874 | 7/1981 | Wolvek et al. . |
| 4,545,390 | 10/1985 | Leary . |
| 4,586,923 | 5/1986 | Gould et al. .................... 604/95 |
| 4,664,114 | 5/1987 | Ghodsian .................... 606/193 |
| 4,726,355 | 2/1988 | Okada . |
| 4,758,221 | 7/1988 | Jureidini .................... 604/95 |
| 4,886,067 | 12/1989 | Palermo .................... 128/772 |
| 4,941,454 | 7/1990 | Wood et al. . |
| 5,035,231 | 7/1991 | Kubokawa et al. .............. 128/653.5 |
| 5,050,607 | 9/1991 | Bradley et al. . |
| 5,102,416 | 4/1992 | Rock .................... 604/95 |
| 5,104,377 | 4/1992 | Levine .................... 606/193 |
| 5,106,381 | 4/1992 | Chikama .................... 128/772 |
| 5,170,789 | 12/1992 | Narayan et al. ............... 128/653.5 |
| 5,190,050 | 3/1993 | Nitzsche .................... 128/772 |
| 5,195,968 | 3/1993 | Lundquist et al. .............. 128/772 |
| 5,199,950 | 4/1993 | Schmitt et al. .................... 128/772 |

FOREIGN PATENT DOCUMENTS 0385367 9/1990 European Pat. Off. .

*Primary Examiner*—K. M. Pfaffle
*Attorney, Agent, or Firm*—Keck, Mahin & Cate

[57] ABSTRACT

An insertable intracavity probe for use in magnetic resonance imaging of an area of interest in a relatively inaccessible region of the body is disclosed. The probe has an internal pickup coil carried at the distal end of a shaft for rectal insertion of the coil and an inflatable anti-migration cuff to hold the probe in position and prevent outward migration thereof during a procedure. The anti-migration cuff is carried on an outer sleeve which is slidably and rotatably mounted on the shaft. The coil is carried on a resilient tip structure at the distal end of the shaft which is flexible in the plane normal to the plane of the coil. Deflection of the coil assembly is controlled by a pair of control lines attached to the distal end of the tip structure. The lines may be selectively tensioned to deflect the coil in the direction of tension by a thumb wheel control at the handle of the probe.

9 Claims, 2 Drawing Sheets

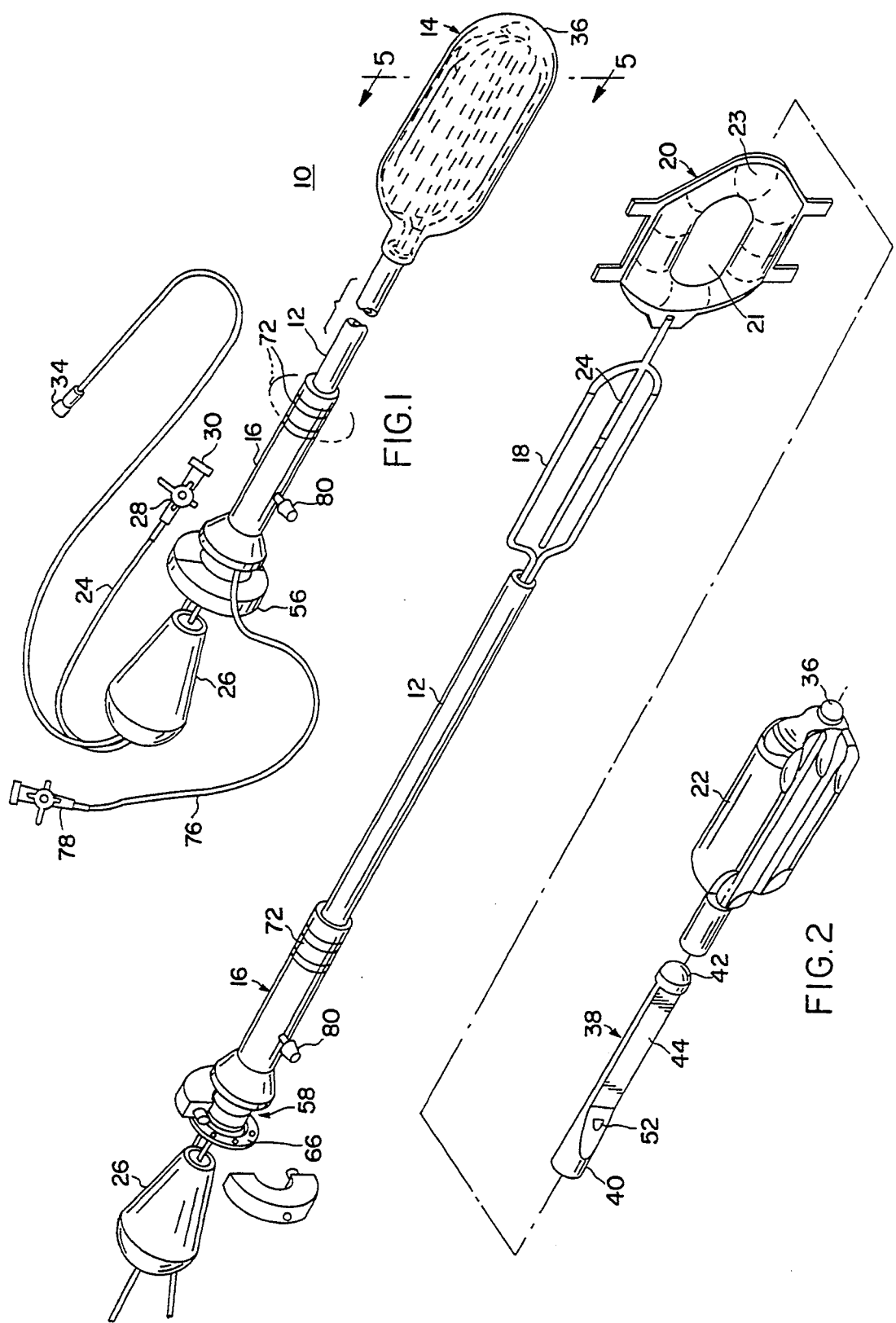

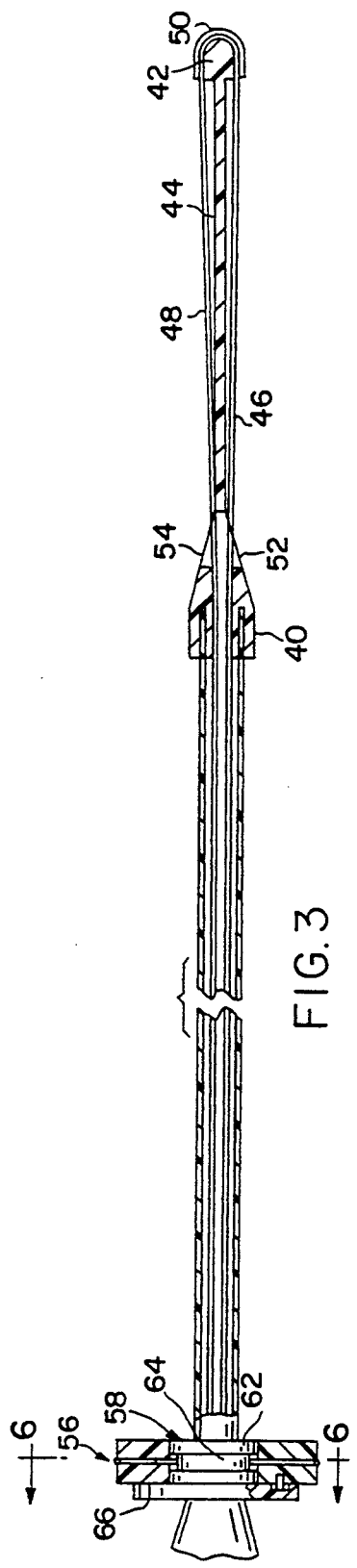
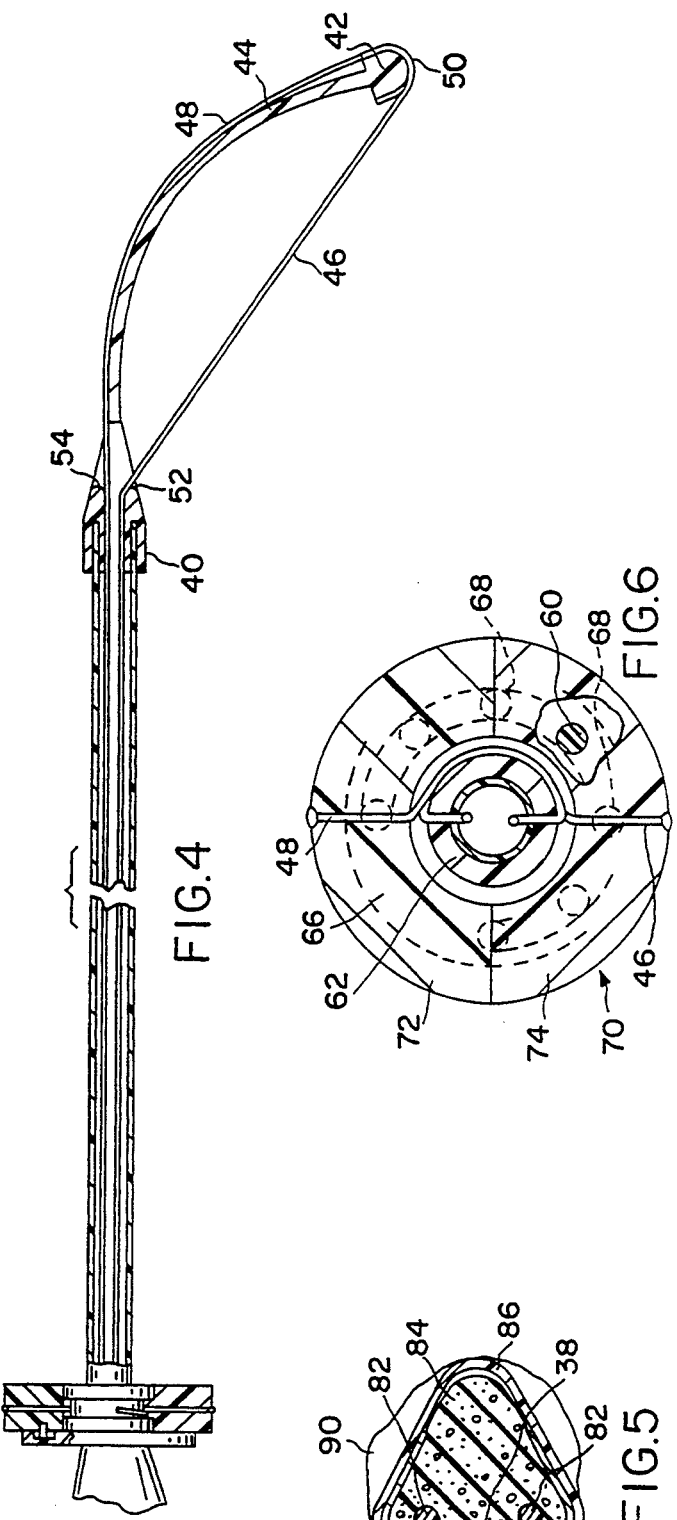

ENDORECTAL PROBE WITH PLANAR MOVEABLE MRI COIL

BACKGROUND OF THE INVENTION

This invention relates to a receiving device in the form of an intracavity probe for use in magnetic resonance imaging (MRI) and spectroscopy systems to enhance the imaging performance and spectroscopy sensitivity of such instruments when evaluating anatomical regions small in size relative to the body, and deep within the body, but proximate a location where an insertable pickup probe may be used. More particularly, the present invention relates to an intracavity pickup probe which is externally directable within the body cavity to allow for optimum placement of the probe relative to the intended target.

In the field of MRI systems, also commonly known as NMR imaging systems, external pickup probes are typically used for receiving radio frequency signals from the anatomical region of interest. See, for example, copending, commonly assigned application Ser. No. 07/771,419, filed Oct. 7, 1991, titled "Probe for MRI Imaging and Spectroscopy Particularly in the Cervical Region" for a discussion of such probes. For optimum performance when imaging certain select parts of the body, the pickup probe should be insertable for intracavity use and include a radio frequency receiving coil to be positioned as close to the region of interest as possible. It is important, therefore, that a suitable MRI probe be provided which may be selectively and accurately positioned within the body cavity proximate the deep body target whose image is sought to be received by the pickup. The internal placement of the pickup, once inserted within the body cavity, must be capable of adjustment and control at the proximal end of the probe, outside the body.

In order to manipulate the MRI probe within the body cavity, it is desirable to have a probe tip which is rotatable and deflectable, in order that the pickup coil may be rotated to the proper orientation within the body cavity, and positioned accurately and firmly against the target region. It is also desirable to be able to direct the probe toward the anatomical area of interest through a body cavity which may curve. It is desirable as well to be able to control the rotation and deflection of the probe tip, and therefore, its orientation, remotely, that is, outside the patient's body.

SUMMARY OF THE INVENTION

It is an object of the present invention to provide an insertable intracavity pickup probe capable of being placed in close proximity to a region of interest to improve the quality of the magnetic resonance image or spectrum.

It is a further object of the present invention to provide an insertable MRI pickup probe which is capable of being accurately directed toward an anatomical area of interest It is a further object of the present invention to provide an insertable MRI pickup probe capable of being accurately positioned relative to an area of interest which is in a relatively inaccessible region of the body such as the cervix, prostate or colon.

Another object of the invention is to provide an insertable MRI pickup probe which, when inserted adjacent a site of interest in a body cavity, can be manipulated from outside the body cavity to advantageously position the MRI coil against the anatomical area of interest.

Another object of the invention is to provide an insertable MRI pickup probe which, when inserted adjacent a site of interest in a body cavity, can be manipulated so as to optimize the position of the MRI coil in relation to the particular area of interest by lateral deflection of the pickup coil.

The invention in a specific embodiment relates to an insertable intracavity pickup probe, and more specifically an intrarectal pickup probe for imaging of the cervix and associated area. Although the pickup probe is described hereinafter as principally intended to image or obtain spectra from the area of the cervix, it should be understood that the concepts outlined are equally appropriate for other regions of interest such as the rectum, vagina, bladder and mouth.

The insertable pickup probe of the present invention comprises a shaft which supports a patient interface balloon structure at its distal end. In a specific embodiment the interface balloon structure contains a receiving coil in the form of a closed substantially planar loop with opposite sides of the loop extending longitudinally relative to the shaft. An internal balloon assembly is positioned within the structure, having inflatable arms each extending outwardly from the shaft and along one of the respective lengthwise sides of the coil, which is suitably attached, as by adhesive strips or the like to the respective balloon arms. The balloon and its associated MRI pickup coil are carried on a flexible tip structure which includes a flexible blade to which the coil and inner balloon are suitably attached. The flexible tip structure has a control line anchor located at its distal end to which a pair of control lines are attached. The control lines lie substantially parallel to the blade of the flexible tip structure, on opposite sides thereof.

The proximal end of the flexible tip structure has guide openings on opposite sides of the proximal end of the blade to receive each of the control lines. The control lines are carried from the guides, within the hollow shaft of the pickup assembly, to a thumb wheel for selectively tensioning one or the other of the control lines.

Rotation of the thumb wheel relative to the shaft will take up onto a bobbin a length of one of the control lines to apply tension to that control line while simultaneously releasing tension on the opposite control line. The tensioned control line will act to deflect the distal anchor tip of the flexible tip structure in the direction of the tensioned cable to deflect the coil assembly in that direction.

The shaft of the probe may be provided with an inflatable annular anti-migration cuff to prevent the probe working out of a body cavity when inserted. The cuff may be fixed in relation to the shaft. In the preferred embodiment the inflatable cuff may be slidable along the shaft on a sleeve. The movable anti-migration cuff allows the depth of insertion of the probe and the rotational orientation of the probe to be varied to suit different size anatomies.

The above and other objects and advantages of the present invention will become more readily apparent when reference is made to the following description taken in conjunction with the accompanying drawing figures.

BRIEF DESCRIPTION OF THE DRAWING FIGURES

FIG. 1 is a perspective view of an insertable pickup probe in accordance with the present invention.

FIG. 2 is an exploded view of the pickup probe of the present invention.

FIG. 3 is a cross-sectional side elevation of the pickup probe with the coil assembly relaxed and aligned with the shaft of the probe.

FIG. 4 is a cross-sectional side elevation of the pickup probe with the coil assembly shown deflected from the original plane of the coil.

FIG. 5 is a cross-sectional view of another embodiment of the present invention as inserted in a colon.

FIG. 6 is a cross-sectional view of the probe embodying the present invention taken along line 6—6 in FIG. 3.

DESCRIPTION OF THE PREFERRED EMBODIMENT

Referring first to FIG. 1, an insertable cervical pickup probe is shown in an assembled form at 10. The pickup probe 10 is an MRI or NMR receiving device capable of imaging or gathering spectra from the human cervix and surrounding tissue. The probe 10 is used with an interface network (not shown) which provides the tuning, impedance matching and decoupling functions in a manner well known in the art. The probe 10 includes a shaft 12 which supports a patient interface coil assembly 14 at its distal end. Anti-migration sleeve assembly 16 is slidably and rotatably mounted on shaft 12. As will be described in more detail later in this embodiment, coil assembly 14 includes an internal pickup coil 18 and an internal inflatable balloon 20, as shown in FIG. 2. The coil and the internal balloon structure are accommodated, as will be described, in outer balloon 22. A tube 24 for inflating the internal balloon extends through shaft 12 and exits at the proximal end of handle 26. The tube has an inflation control stopcock 28 and a connection 30 for attaching the tube to the nozzle of a suitable air pump, such as a syringe, not shown.

The receiving coil contained within the coil assembly 14 can be electrically connected to an interface network by an insulated interconnecting cable 32 which has a connecting plug 34 at its proximal end.

The outer balloon 22 of the coil assembly 14, in order to facilitate rectal insertion and accommodation to portions of the female anatomy adjacent to the cervix is of a generally elongate form. The outer balloon is formed of suitable elastic material and has a distal end nipple 36 accommodating the end of the flexible tip structure 38 at the distal end of shaft.

Coil 18 is carried on flexible tip structure 38 which includes base section 40, tip section 42 and resilient center blade section 44. Blade section 44 is aligned substantially coplanar to coil 18 and is flexible in a plane normal to the plane of the coil. The coil assembly, therefore, is flexible in that direction only and stiffened against deflection in the plane of the coil.

A pair of control lines 46 and 48 are attached at their distal ends to an anchor 50 on tip section 42 of flexible tip structure 38. The control lines 46 and 48 are disposed longitudinally along opposite sides of blade 44 through guides 52 and 54, respectively which are openings in base section 44. Guides 52 and 54 communicate with the interior of shaft 12. Control lines 46 and 48 pass through shaft 12 to thumb wheel assembly 56.

Thumb wheel assembly 56 illustrated in FIG. 6, includes annular bobbin 58 which is fixed to shaft 12 adjacent handle 26. Bobbin sleeve 62 includes annular groove 64 and bobbin flange 66. Bobbin flange 66 includes detents 68. Thumb wheel ring 70, formed of two semi-circular ring halves 72 and 74, includes pin 60, which is selectively matable with any of detents 68 in bobbin flange 66.

The proximal end of each of the control lines 46 and 48 is attached to the inner concave face of one-half of thumb wheel ring 70. Control lines 46 and 48 are wound in opposite directions around bobbin sleeve 62.

When the thumb wheel 56 is at its median position, tension is evenly applied to each of control lines 46 and 48 as shown in FIGS. 3 and 6.

Rotation of thumb wheel 70 in clockwise direction about bobbin sleeve 62 applies tension to one control line while the other control line is released. Opposite rotation of thumb wheel 70 releases the control line previously tensioned and applies tension to the other control line.

Tension applied to one of control lines 46 pulls on tip assembly 42 from guide 52 as shown in FIG. 4. This acts to deflect blade 44 and coil 18 in the direction of the tension applied.

FIG. 1 shows migration cuff 72 which can be selectively adjusted along shaft 12 on a sliding sleeve 16. Inflatable cuff 72 is connected to inflation tube 76 which extends into the interior of sleeve 16. Tube 76 is provided with a stopcock 78 which can be connected to an inflation pump.

When the probe is inserted in a body cavity, cuff 72 on sleeve 16 can be inflated from its normal flat state into a distended balloon-like doughnut (illustrated in phantom) to prevent outward migration of the probe. The probe may be adjusted longitudinally within the sleeve 16 to adjust the depth into which the probe is inserted in the body cavity. The shaft 12 of the probe may then be rotated within sleeve 16 to align coil 18 rotationally within the body cavity. When the appropriate depth of insertion and rotational orientation has been achieved, shaft 12 may be locked in position within sleeve 16 by set screw 80.

For ease of introduction of the probe though somewhat convoluted body cavities, the coil assembly may be remotely deflected to pass bends in the cavity passage.

After the probe has been inserted and adjusted for rotational orientation and depth, the coil assembly may be selectively deflected in the plane normal to the plane of the coil to position coil assembly 18 against, or in close proximity to, the anatomical area of interest. The coil may be selectively deflected and locked into deflected position by means of detents 68 and pin 60 on thumb wheel assembly 56.

It should be noted that different embodiments of coil assembly 14 are properly used depending on the intended area of anatomical interest. For example, in the embodiment shown in FIG. 1, the inner balloon 20 may be inflated through tube 24 to expand coil 18 within outer balloon 22. Center area 21 of inner balloon 20 is sealed to define peripheral channel 23 in inner balloon 20. When inflated, channel 23 expands to a doughnut shape (illustrated in phantom) which is appropriate to accommodate the contour of the female cervix. Upon expansion of the coil, the coil may be deflected by adjustment of thumb wheel 70 to grip the cervix.

In another embodiment, shown in FIG. 5, intended as a probe for imaging lesions in the colon, the coil 82 may be carried on a longitudinally extending triangular section of non-inflatable foam material 84 within outer balloon 86. A non-inflatable probe is desirable in this application since inflation and expansion of such probe would compress the layers of the colon wall. This would not be desirable since most lesions occur between these layers, and compression of the layer might render such lesions difficult to appreciate. The three longitudinal edges of the triangular section of foam 84 would contact and compress the colon wall only at the three apexes of the triangular section. Since pickup coil 82 is mounted on one side of the triangular foam on the flexible tip structure 38, in this embodiment, the coil's area of recognition 88 is substantially undisturbed, allowing for recognition of lesions in colon wall 90.

While the invention has been described in connection with preferred embodiments, it will be understood that it is not intended to limit the invention thereto, but it is intended to cover all modifications and alternative constructions falling within the spirit and scope of the invention as expressed in the appended claims.

We claim:

1. An insertable intracavity probe for use in magnetic resonance imaging of a region of interest within a body cavity comprising an elongate shaft having a proximal end, a distal end, a handle on the proximal end of the shaft, and a balloon structure on the distal end of the shaft, the balloon structure including an outer balloon, a pickup coil in the outer balloon lying in a plane, the probe further comprising an electrical lead for connecting the coil to an interface network, and means connected to the coil within the outer balloon for selectively deflecting the coil in a plane normal to the plane of the coil, wherein the balloon structure includes an inner elongate member having a substantially triangular cross-section attached to said deflecting means, and said coil is mounted to one side of said member.

2. An insertable intracavity probe for use in magnetic resonance imaging of an anatomical area of interest within a body cavity, comprising an elongate shaft having a proximal and a distal end, a handle on the proximal end of the shaft, and a balloon structure on the distal end of the shaft, the balloon structure including an outer balloon, a pickup coil in the outer balloon lying in a plane, and at least one internal balloon for controlling the shape of the pickup coil by selective inflation, wherein the internal balloon includes a sealed center area defining a peripheral channel, which, when inflated, will accommodate the anatomical area of interest, the probe further comprising an electrical lead for connecting the coil to an interface network, means for inflating the internal balloon, and means connected to the coil within the outer balloon for selectively deflecting the coil in a plane normal to the plane of the coil.

3. A probe as in claim 2, wherein the deflecting means comprises a resilient tip structure having a resilient blade aligned substantially coplanarly with said pickup coil.

4. A probe as in claim 2 including control means mounted on said shaft adjacent said handle for selectively controlling deflection of said tip structure.

5. A probe as in claim 4 wherein said control means include a thumb wheel rotatably mounted on said shaft, a pair of control lines each having a proximal end connected to said thumb wheel and a distal end connected to said tip structure whereby rotation of said thumb wheel will apply tension to one of said control lines to pull said tip structure out of planar alignment.

6. A probe as in claim 2 including a selectively inflatable anti-migration cuff structure on the shaft for inflation from a substantially flat configuration into a distended doughnut-like configuration around the shaft when the probe is inserted in the body cavity to prevent outward migration of the probe from the cavity.

7. A probe as in claim 2 wherein the anatomical area of interest is the cervix.

8. A method of magnetic resonance imaging a region of interest internally of a patient comprising providing the insertable intracavity probe according to claim 2, further comprising inserting the balloon structure of the probe into the body cavity of a patient, using said deflecting means to facilitate navigation through the body cavity until the coil is proximate said region of interest and inflating the internal balloon such that the peripheral channel is positioned adjacent said region of interest.

9. A method as in claim 8 wherein said area of interest is the cervix and said body cavity is the rectum.

* * * * *